(12) United States Patent
Fonnum et al.

(10) Patent No.: US 8,038,987 B2
(45) Date of Patent: Oct. 18, 2011

(54) PROCESS FOR THE PREPARATION OF COATED POLYMER PARTICLES

(75) Inventors: Geir Fonnum, Fjelhamar (NO); Nini Kjus Hofsløkken, Oslo (NO); Elin Marie Aksnes, Oslo (NO); Lars Kilaas, Trondheim (NO); Arvid Trygve Berge, Trondheim (NO); Per Stenstad, Trondheim (NO); Ruth Schmid, Tiller (NO); Jon Olav Bjorgum, Heimdal (NO); Tom-Nils Nilsen, Ramheim (NO)

(73) Assignee: Invitrogen Dynal AS, Oslo (NO)

( * ) Notice: Subject to any disclaimer, the term of this patent is extended or adjusted under 35 U.S.C. 154(b) by 1256 days.

(21) Appl. No.: 11/563,598

(22) Filed: Nov. 27, 2006

(65) Prior Publication Data

US 2007/0098639 A1    May 3, 2007

Related U.S. Application Data

(62) Division of application No. 11/071,720, filed on Mar. 3, 2005, now Pat. No. 7,160,707, which is a division of application No. 10/834,391, filed on Apr. 28, 2004, now Pat. No. 6,986,913.

(60) Provisional application No. 60/488,020, filed on Jul. 17, 2003.

(51) Int. Cl.
| | |
|---|---|
| A61B 5/055 | (2006.01) |
| A61K 9/14 | (2006.01) |
| A61K 9/16 | (2006.01) |
| C12N 11/08 | (2006.01) |
| B05D 7/00 | (2006.01) |
| B05D 3/02 | (2006.01) |
| B32B 19/00 | (2006.01) |
| B32B 5/16 | (2006.01) |
| B32B 27/38 | (2006.01) |
| C08G 73/02 | (2006.01) |
| C08L 71/02 | (2006.01) |

(52) U.S. Cl. ............ 424/9.322; 424/9.3; 424/9.32; 424/489; 424/490; 424/497; 435/180; 427/212; 427/222; 427/372.2; 427/385.5; 428/357; 428/403; 428/407; 428/413; 525/185; 525/187

(58) Field of Classification Search ............ 424/489, 424/490, 497, 501, 9.3, 9.32, 9.322; 435/180; 427/212, 222, 372.2, 385.5; 428/357, 403, 428/407, 413; 525/185, 187
See application file for complete search history.

(56) References Cited

U.S. PATENT DOCUMENTS

| | | | |
|---|---|---|---|
| 4,054,452 A | 10/1977 | Schlesinger et al. | |
| 4,352,884 A | 10/1982 | Nakashima et al. | |
| 4,654,267 A | 3/1987 | Ugelstad et al. | |
| 4,827,945 A | 5/1989 | Groman et al. | |
| 5,091,206 A | 2/1992 | Wang et al. | |
| 5,763,203 A * | 6/1998 | Ugelstad et al. | 435/7.24 |
| 6,133,047 A | 10/2000 | Elaissari et al. | |
| 6,797,782 B2 * | 9/2004 | Ozaki et al. | 525/244 |
| 2002/0169293 A1 | 11/2002 | Handa et al. | |

FOREIGN PATENT DOCUMENTS

| | | |
|---|---|---|
| AU | 2003288454 | 6/2004 |
| JP | 49-110402 | 10/1974 |
| JP | 03505163 | 11/1991 |
| JP | 07082302 | 3/1995 |
| WO | WO-89/04373 | 5/1989 |
| WO | WO-90/10696 | 9/1990 |
| WO | WO-96/40502 | 12/1996 |
| WO | WO-99/19375 | 4/1999 |
| WO | WO-00/61648 | 10/2000 |
| WO | WO-01/70825 A1 | 9/2001 |
| WO | WO 02/99425 * | 12/2002 |
| WO | WO-2004/053490 | 6/2004 |

OTHER PUBLICATIONS

Database WPI Section Ch, Week 197523 Derwent Publications Ltd., London, GB; AN 1975-38299W XP002299991 & JP 49110402 A (Asahi Chem Ind Co Ltd) (Oct. 21, 1974).
International Preliminary Examination Report, PCT/GB2004/001801, Apr. 10, 2005.
CA Application No. 2532711, Office Action mailed Jan. 4, 2011.
CN Application No. 2004800263891, Office Action mailed Feb. 1, 2011.
CN Application No. 2004800263891, Response to Feb. 1, 2011 Office Action filed Apr. 15, 2011.

* cited by examiner

*Primary Examiner* — Michael G Hartley
*Assistant Examiner* — Leah Schlientz

(57) ABSTRACT

A process for the preparation of coated polymer particles containing superparamagnetic crystals, said process comprising reacting porous, surface-functionalized, superparamagnetic crystal-containing polymer particles of diameter 0.5 to 1.8 μm with at least one polyisocyanate and at least one diol or at least one epoxide.

9 Claims, No Drawings

PROCESS FOR THE PREPARATION OF COATED POLYMER PARTICLES

CROSS-REFERENCES TO RELATED APPLICATIONS

This application is a divisional application of U.S. patent application Ser. No. 11/071,720, now U.S. Pat. No. 7,160,707, filed Mar. 3, 2005, which is a divisional of U.S. patent application Ser. No. 10/834,391, now U.S. Pat. No. 6,986,913, filed Apr. 28, 2004, which claims priority to U.S. Provisional Patent Application No. 60/488,020, filed Jul. 17, 2003, the contents of which are each incorporated by reference as if set forth fully herein.

FIELD OF THE INVENTION

This invention relates to a process for the preparation of coated magnetic polymer particles.

BACKGROUND OF THE INVENTION

Magnetic polymer particles are of general utility in various medical and biochemical fields, for example as transport vehicles for the delivery of pharmaceutical products, for diagnostic purposes, for separation and for synthetic purposes. Such particles rely upon their magnetic properties in order to perform these functions. In diagnostic assay applications, for example, application of a magnetic field to a sample containing an analyte bound to magnetic polymer particles allows the isolation of the analyte without the use of centrifugation or filtration and in therapeutic applications, for example, application of a magnetic field to the patient may serve to target drug-carrying magnetic polymer particles to a desired body site.

By magnetic is meant herein that the polymer particles contain superparamagnetic crystals. Thus the magnetic polymer particles are magnetically displaceable but are not permanently magnetizable. Many processes for preparing magnetic polymer particles are known, a large number of which involve preparing maghemite- or magnetite-containing polymer particles from pre-formed magnetic iron oxides, e.g. magnetite. Some of processes involved are described in U.S. Pat. No. 4,654,267 (Ugelstad) the contents of which are incorporated herein by reference.

Thus U.S. Pat. No. 4,654,267 outlines a number of limitations with regard to the processes which preceded it; these include difficulty in obtaining magnetic particles of similar size and/or of homogeneous or uniform magnetic properties, as well as a more general problem relating to the difficulty of incorporating magnetic material inside the cavities of porous polymer particles.

With deposition taking place principally on the surface, or in large open cavities, leaching of magnetic particles, which shortens the useful lifetime of magnetic polymer particles in the applications to which they are put, was consequently problematic.

In order to overcome these disadvantages, U.S. Pat. No. 4,654,267 proposed a preparative method whereby, in its simplest form, porous polymer particles are impregnated with solutions of iron compounds whereafter the iron is precipitated, for instance by raising the pH value. The precipitated iron compounds may then be converted to superparamagnetic iron oxide crystals by heating.

To produce porous magnetic polymer particles having magnetic material disposed within the polymer pores, U.S. Pat. No. 4,654,267 advocated the use of porous polymer particles having surface functional groups which serve to draw the iron ions into the polymer particles. These functional groups could either result from the use of functionalized comonomers in the production of the polymer or from post-polymerization treatment of the polymer to introduce the functional groups, e.g. by coupling to or transformation of existing groups on the polymer surface.

Whilst the invention disclosed in U.S. Pat. No. 4,654,267 does in part solve the problem of producing magnetic polymer particles which have more homogeneous magnetic properties, the problem of leaching of the superparamagnetic crystals from the polymer particles remains.

SUMMARY OF THE INVENTION

We have now surprisingly discovered that for particles of a certain size, this problem may be solved and magnetic particles with particularly suitable surface characteristics may be produced by reacting surface functionalized, magnetic polymer particles with a combination of polyisocyanate/diol or epoxide monomers to produce a "coated" magnetic polymer particle.

Viewed from a first aspect, therefore, the present invention provides a process for the preparation of coated polymer particles containing superparamagnetic crystals, said process comprising reacting porous, surface-functionalized, superparamagnetic crystal containing polymer particles of diameter 0.5 to 1.8 µm, more preferably of diameter 0.75 to 1.2 µm, especially approximately 1 µm, with at least one, preferably at least two epoxide compounds.

Viewed from a second aspect, the present invention provides a process for the preparation of coated polymer particles containing superparamagnetic crystals, said process comprising reacting porous, surface-functionalized, superparamagnetic crystal containing polymer particles of diameter 0.5 to 1.8 µm, e.g. 0.75 to 1.2 µm, especially approximately 1 µm, with at least one polyisocyanate, e.g. diisocyanate, and at least one, preferably at least two, diols.

DETAILED DESCRIPTION OF THE INVENTION

Preferred diols are polyethylene glycols or are of formula $HO((CH_2)_mO)_nH$ (where n is an integer of 1 to 15, e.g. 2 to 10, preferably 2 to 4, and m is an integer of 2 to 6, preferably 2 to 3, most preferably 2). Where only one diol is employed, this is preferably a polyethylene glycol, e.g. polyethylene glycol 300, 400, 500 or 600.

The porous polymer particles used in the process of the invention may be any porous polymer having a functionalized surface, e.g. as described in U.S. Pat. No. 4,654,267.

The surface functionality on the polymer is preferably a group capable, optionally with activation, of reacting with a polyisocyanate or epoxide to covalently bond the polyisocyanate or epoxide to the surface. Most preferably the surface is amine functionalized.

The polymer is preferably made from combinations of vinylic polymers, e.g. styrenes, acrylates and/or methacrylates. The polymeric material may optionally be crosslinked, for example by incorporation of cross-linking agents, for example as comonomers, e.g. divinylbenzene (DVB) or ethyleneglycol dimethacrylate. Particles comprising DVB are preferred.

Appropriate quantities of the cross-linking agents (e.g. comonomers) required will be well known to the skilled man. Preferably the polymer is a cross-linked styrenic polymer (e.g. a styrene-divinylbenzene polymer, which may be surface functionalized by the use of a nitro-group containing comonomer, e.g. nitro-styrene, and subsequent reduction) or a cross-linked (meth)acrylic polymer surface functionalized by the use of an epoxy-group containing comonomer (e.g. glycidylmethacrylate) and subsequent amination (e.g. by reaction with ethylene diamine).

The superparamagnetic crystals in the polymer particles used in the process of the invention may be of any material capable of being deposited in superparamagnetic crystalline form in the porous polymer particles. Magnetic iron oxides, e.g. magnetite or maghemite are preferred; however the crystals may be of mixed metal oxides or other magnetic material if desired. The total quantity of crystalline magnetic material present is generally more than 1%, preferably more than 3%, desirably more than or equal to 5% (by weight, e.g. up to 40% wt. The percentage is calculated on a Fe (or equivalent metal in the case of magnetic materials other than iron oxides) weight basis based upon the overall dry weight of the coated particles.

Polymer particles according to the present invention will have sizes (i.e. diameters) that are generally in the range 0.5 to 1.8 μm, e.g 0.75 to 1.2 μm, preferably 0.9 to 1.1 μm.

Typically the porous particles used will have a surface area of at least 15 m5/g (measured by the BET nitrogen absorption method), and more preferably at least 30 m5/g, e.g. up to 700 m5/g, when corrected to a mean particle diameter of 2.7 μm (i.e. multiply surface area by 2.7/MD, where MD is the mean diameter in micrometers). Similarly scaled, the particle pore volume is preferably at least 0.1 mL/g.

Typically, the polymer particles are spherical and substantially monodisperse before they are coated and especially preferably remain spherical and substantially monodisperse once they have been coated.

By substantially monodisperse it is meant that for a plurality of particles (e.g. at least 100, more preferably at least 1000) the particles have a coefficient of variation (CV) of less than 20%, for example less than 15%, preferably less than 12%, more preferably less than 11%, still more preferably less than 10% and most preferably no more than about 8%, e.g. 2 to 5%. CV is determined in percentage as $$CV = \frac{100 \times \text{standard deviation}}{\text{mean}}$$

where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyzer.

Of particular utility in the present invention are polymeric particles disclosed in WO 99/19375 (Dyno Industrier ASA), WO 00/61648 (Dyno Specialty Polymers AS) made in part from amino styrene as disclosed in WO 01/70825, the contents of which are incorporated herein by reference.

Alternatively, in contrast to the disclosure of WO01/70825, functionalisation of the polymeric material may take place after polymerisation by, for example, nitration and subsequent reduction of the thus-formed nitro groups to pendant amine groups; or direct amination, for example by treatment with amino ethanol. As further alternatives, polymeric particles prepared by the well-known Ugelstad two-step swelling process and the improvements thereto disclosed in WO 00/61647 (Dyno) may be used. Also of use here are polymeric particles prepared by the processes disclosed in WO99/19375 and WO00/61648. Porous polymer particles produced according to the processes described in these publications may have magnetic particles deposited in their pores by standard techniques, e.g. as described above. As a further possibility, porous polymer particles may be prepared from nitro styrene and DVB, and magnetic material introduced as taught in U.S. Pat. No. 4,654,267. Of all these processes, the use of amino styrene, particularly 4-aminostyrene, as monomer or comonomer in the preparation of amino-bearing polymeric material is preferred. Use of this monomer or comonomer obviates the need for post-polymerisation nitration and reduction reactions. Moreover, the more predictable nature (homogeneity) of the coating afforded by this process permits a more reliable coating to be applied.

The reaction of the porous magnetic polymer particle with the epoxides or polyisocyanates generates a polymer within the pores of the polymer particles which serves essentially to block these pores physically encapsulating the superparamagnetic crystals within the polymer particles. The resulting "coated" particles then have reduced porosity relative to the porous starting material. Surprisingly we have found that the superparamagnetic crystals appear to catalyse the polymerization so that the coating forms preferentially in their vicinity.

If desired, an epoxide polymer coating may be cross-linked, e.g. by use of an isocyanate or diisocyanate in known fashion. Equally if desired further materials may be impregnated into the porous particles either before the coating polymerization reaction or after coating polymerization but before coating polymer cross-linking. Typically such further materials will be radiation emitters or absorbers, e.g. chromophores, fluorophores or radioactively labelled materials.

The particles may be reacted with a single epoxide to form the coating. Suitable epoxides here include glycidol, allylglycidyl ether or glycidylmethacrylate. In particular, a coating reaction involving glycidylmethacrylate in combination with iron (III) chloride has provided advantageous coatings.

However, in a preferred embodiment, the porous polymer particles are reacted with a mixture of epoxides, e.g. 2-6 epoxides, especially 2, 3 or 4 epoxides. Of these, diepoxides or polyepoxides preferably constitute at least 30 mole %, more preferably at least 45 mole %.

The epoxide compounds used according to the invention preferably comprise at least one diepoxide, e.g. a combination of two diepoxides or of a monoepoxide and a diepoxide. Preferably, the epoxides contain at least one ether link and optionally a hydrophobic component, e.g. a $C_{4-10}$ alkylene chain or a phenyl or bisphenyl group. Generally, the epoxides will have a carbon atom content of from 3 to 50, preferably 3 to 25.

Typical epoxides that may be used include epichlorohydrin, epibromohydrin, isopropylglycidyl ether, butyl glycidyl ether, allylglycidyl ether, 1,4-butanediol diglycidyl ether (1,4-bis(2,3-epoxypropoxy)butane), neopentylglycol diglycidyl ether, ethylene glycol diglycidyl ether, polyethylene glycol diglycidyl ether (e.g. of Mw 150 to 1000 g/mol), glycerol diglycidyl ether, glycerolpropoxylate triglycidylether, glycidol, glycidyl methacrylate, and epoxides based on bisphenol A or bisphenol F, e.g. 2,2-bis(4-(2,3-epoxypropoxy)phenyl)-propane.

Especially preferred epoxides include 2,2-bis(4-(2,3-epoxypropoxy)phenyl)-propane, allylglycidyl ether, 1,4-butanediol diglycidyl ether and glycidol. In particular, the epoxides sold under the Araldite trade name are favoured, e.g. Araldite LY-564 (a mixture of 2,2-bis(4-(2,3-epoxypropoxy)

phenyl)-propane and 1,4-butanediol diglycidyl ether) and Araldite LY-026 (80% pure 1,4-butanediol diglycidyl ether).

It is within the scope of the invention for a first coating reaction to be carried out using a single epoxide and a secondary coating reaction to be carried out using a mixture of at least two epoxides.

In another preferred embodiment, the coating polymer is formed from one or more (e.g. 1, 2 or 3) polyisocyanates and one or more (e.g. 2, 3 or 4) diols. Preferably, one polyisocyante should be employed, e.g. one diisocyanate. Alternatively, a mixture of closely related polyisocyanates can be employed (e.g. Desmodur).

Typical polyisocyanates which may be used include methylene diisocyanate, hexamethylene diisocyanate, 2,4-toluene diisocyanate (2,4-TDI) (and isomers or mixtures thereof), isophorone diisocyanate (IPDI), 4,4'-oxybis(phenylisocyanate), 4,4'-diphenylmethane diisocyanate (MDI), mixtures of MDI and oligomers based on MDI (e.g. Desmodur VL), 2,4-diphenyldiisocyanate, methylene biscyclohexyl diisocyanate ($H_{12}$MDI), phenylene diisocyanate (p-PDI), trans-cyclohexane-1,4-diisocyanate (CHDI), 1,6-diisocyanatohexane (DICH), 1,5-diisocyanato-naphthalene (NDI), paratetramethylxylene diisocyanate (p-TMXDI) or metatetramethylxylene diisocyanate (m-TMXDI).

An especially preferred isocyanate is MDI or polyisocyanates based thereon (e.g. Desmodur). Desmodur comprises MDI and oligomers thereof comprising MDI with $CH_2$-phenylisocyanate residues. The Desmodur is thus a mixture of various polyisocyanates deriving from MDI. A sample structure may be
4,4-methylene bis(phenylisocyanate) 40-50%
4,4-methylene bis(phenylisocyanate)+benzylisocyanate: 20-25%
4,4-methylene bis(phenylisocyanate)+2 benzylisocyanate: 10%
4,4-methylene bis(phenylisocyanate)+3 benzylisocyanate: 2%.

(In a reaction like this the product also contains some of the 2-isomer). The compound is sold by Shell under the trade name Caradate and under the trade names Hylene and Rubinate by Huntsman.

Preferably two diols should be employed. The diols are preferably used in a molar ratio of 0.5:1 to 1:0.5, more preferably 0.8:1 to 1:0.8 when two diols are used. Preferably no one diol is used in a quantity exceeding 90% mol. of the diol mixture.

Preferred diols include diethylene glycol, tetraethylene glycol and polyethylene glycols e.g PEG 300, 400 or 600. A preferred dial combination is diethylene glycol and tetraethylene glycol.

During the coating reaction involving the polyisocyanate, it is preferred if, in a first stage the polyisocyanate is in excess (e.g. relative to any dial). It is within the scope of the invention to use only polyisocyante in this step of the coating procedure. This is believed to minimise the possibility of gelling occurring during the reaction. Where a large excess of polyisocyante is employed in an initial coating reaction, it may then be necessary to react, in a second stage, the coated particles with further diol(s) (e.g. a dial as described above) to react with any unreacted isocyanate groups. Where the initial coating reaction uses polyisocyanate alone, it is essential that the resulting particle is reacted with at least one dial thereafter.

In such an embodiment, such a dial is preferably a polyethylene glycol. The long chain of the PEG dial allows the formation of a sizable linker between the particle coating surface and hence makes easier reaction with affinity ligands such as streptavidin.

It is thus within the scope of the invention to react the particles with polyisocyanate followed by dial, i.e. a stepwise process, to effect coating.

Typically therefore, the coating reaction may be effected by impregnating the porous magnetic polymer particle with the epoxides or the polyisocyanate and diol(s), e.g. using a solution of these (for example in an organic solvent such as methanol or diglyme) or by mixing a dispersion of the porous particles in an organic solvent with a liquid epoxide or diol/polyisocyanate mixture. Sonication may be used to improve impregnation and the reaction may be accelerated by raising the temperature, e.g. to 50-100° C. Any solvent used may be extracted by application of sub-ambient pressure.

Generally, the uses to which magnetic polymer particles are put, e.g. their use as diagnostic tools, require an appropriate degree of electrophilicity in order that they may participate adequately in coupling and other reactions in aqueous systems prevalent in biological media.

Whilst the general polarity of the coatings is desirably electrophilic, certain coatings which contain hydrophobic moieties may be incorporated so as to tailor the degree of electrophilicity to that which is desired. In this way, the invention permits the provision of useful diagnostic and other tools having a wide range of polarities.

If desired, in the process of the invention, the surfaces of the coated magnetic polymer particles may be further functionalised, e.g. by coupling a drug molecule, a reporter label (e.g. a chromophore, fluorophore, enzyme or radiolabel), or a ligand (e.g. an antibody or antibody fragment, a metal ion complexing agent, a member of a specific binding partner pair (e.g. biotin or streptavidin), an oligopeptide, an oligonucleotide, or an oligosaccharide).

Such coupling may be direct or indirect (and so may or may not involve the use of a coupling agent to form a linkage between the particle and the substance being coupled to it) and may be biodegradable or non-biodegradable. Biodegradable couplings may be desired if the magnetic polymer particles are to be used for the targeted release of an active compound. Accordingly after coating has been effected, the pendent groups of the coating may be manipulated to provide appropriate functionality (for example epoxy, hydroxy, amino etc. functionalities) for the attachment of such substances.

The functionalised coated magnetic particle may be bound to an affinity ligand the nature of which will be selected based on its affinity for a particular analyte whose presence or absence in a sample is to be ascertained. The affinity molecule may therefore comprise any molecule capable of being linked to a magnetic probe which is also capable of specific recognition of a particular analyte. Affinity ligands therefore include monoclonal antibodies, polyclonal antibodies, antibody fragments, nucleic acids, oligonucleotides, proteins, oligopeptides, polysaccharides, sugars, peptides, peptide encoding nucleic acid molecules, antigens, drugs and other ligands. Examples of suitable affinity ligands are available in the published literature and are well known. The use of further binding partners, secondary affinity ligands and linking groups which is routine in the art will not be discussed further herein although it will be appreciated that the use of such species with the particles of the invention is possible if desired.

In an especially preferred embodiment, the particle coating is prepared using an epoxide compound having a functional group copolymerizable with an acrylate, e.g. a carbon-carbon double bond, for example using two or three epoxides one of which contains an unsaturated carbon-carbon bond. The coated particles may then be functionalized by reaction with a vinyl or acrylic monomer carrying a functional group, for example a carboxylic acid group (e.g. using acrylic acid). Further functionalization may then readily be achieved by reaction of the pendant carboxyl groups, e.g. by reaction with N-hydroxysuccinimide or with streptavidin. This process and particles formed by it are novel and form a further aspect of the invention.

Thus viewed from a further aspect the invention provides coated polymeric particles, optionally carrying superparamagnetic crystals, having a coating formed from at least two epoxides, at least one of which having an unsaturated carbon-carbon bond copolymerizable with an acrylic monomer.

Viewed from another aspect the invention provides a process for the preparation of coated polymer particles, optionally containing superparamagnetic crystals, said process comprising reacting porous, surface-functionalized, optionally superparamagnetic crystal-containing polymer particles with at least two epoxide compounds, at least one of which having an unsaturated carbon-carbon bond copolymerizable with an acrylic monomer; and reacting the formed particles with a vinylic monomer, (e.g. allylglycidyl ether or an acrylic monomer, e.g. acrylic acid or acrylamide). The resulting particles may then be further reacted with an affinity ligand e.g. streptavidin. The particles formed in this process form a still further aspect of the invention.

Viewed from a further aspect the invention provides the use of particles of the invention in syntheses, extractions or assays, in particular in nucleic acid detection.

Epoxides of use in this aspect include glycidylmethacrylate and allylglycidylether.

Introduction of vinyl groups polymerisable with, for example, an acrylic acid can also be achieved by reacting the coating surface with a compound such as methacrylic anhydride. For example, a coated particle comprising a coating formed from the reaction of two epoxides which is washed (e.g. in NaOH) to expose hydroxyl functionalities would react readily with methyl acrylic anhydride to allow the introduction of vinyl groups to the polymer surface.

As mentioned above, the nature of the external substance coupled to the particles may be selected on the basis of its ability to bind to a particular target material. Nucleic acid detection generally involves probing a sample thought to contain target nucleic acids using a nucleic acid probe that contains a nucleic acid sequence that specifically recognises, e.g. hybridises with, the sequence of the target nucleic acids, such that the nucleic acid affinity ligand and the target nucleic acids in combination create a hybridisation layer. Suitably functionalised particles of the invention, e.g. those coated with at least two epoxides and carrying a carboxyl group subsequently reacted with streptavidin, are ideally suited for nucleic acid detection.

Biotinylated single strand oligonucleotide probes bound to streptavidin beads can be used to isolate sequence specific DNA. The biotinylated probes are bound to the beads by mixing the appropriate amount of beads with an excess of biotinylated probe. The beads/probe are then incubated with the DNA sample in a hybridisation buffer, e.g. SSPE or SSC, under conditions appropriate for the length and sequence of the probe and DNA. The excess and unwanted DNA is washed away utilizing the magnetic properties of the beads. The captured DNA can be detected/quantified by PCR etc.

Biotinylated double strand DNA fragments bound to streptavidin beads can be used to isolate DNA sequence specific binding proteins. The biotinylated DNA is bound to the beads by mixing the appropriate amount of beads with an excess of biotinylated DNA fragments. The beads/DNA are then incubated with the protein sample in a hybridisation buffer, under conditions appropriate for the protein under investigation. The excess and unwanted protein is washed away utilizing the magnetic properties of the beads. The captured protein can be eluted from the probe (by high salt, low salt, heat, low pH etc) for downstream applications and detection.

The target material may optionally be a material of biological or synthetic origin, e.g. it may be a molecule or a group of molecules, including for example antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatised nucleic acids, DNA, RNA, natural or synthetic drugs, receptors, virus particles, bacterial particles virus components, cells, cellular components, natural or synthetic lipid vesicles, polymer membranes, polymer services and particles and glass and plastic surfaces.

Where the beads of the invention are to be employed in immunoassays it has surprisingly been found that tosylation of the particles after coating results in particles which exhibit improved performance in immunoassays. Thus, in a preferred embodiment, particles carrying a coating can be tosylated, e.g. by reaction of the particles with tosylchloride in the presence of a base. The resulting tosylated coated particles are new and form a further aspect of the invention. By tosyl is meant a toluene-4-sulphonyl group.

Moreover, such tosylated species can be readily reacted with affinity ligands, e.g. streptavidin to form still further new particles.

Thus viewed from a further aspect, the invention provides coated polymeric particles, carrying superparamagnetic crystals, having a coating formed from at least one polyisocyanate and at least one diol, which is subsequently tosylated, e.g. by reaction with tosyl chloride and optionally then reacted with an affinity ligand, e.g. streptavidin.

Viewed from another aspect, the invention provides coated polymeric particles, optionally carrying superparamagnetic crystals, having a coating formed from at least one epoxide, which is subsequently tosylated, e.g. by reaction with tosyl chloride, and optionally then reacted with an affinity ligand, e.g. streptavidin.

Moreover, it has surprisingly been found that particles of the diameters claimed herein have a greatly increased capacity for binding compared to beads of greater size, e.g. 3 μm beads. It is envisaged that the binding capacity of the claimed beads is over 200% greater than that of larger beads allowing the use of considerably lower amounts particles in an assay procedure.

The beads of the invention are therefore of utility in adsorption/desorption processes analogously to the mechanisms in Reversed Phase chromatography or hydrophobic interaction chromatography. Reversed phase chromatography is a separation technique that utilises a hydrophobic adsorption interaction between a solute molecule (e.g. a protein) and an immobilised hydrophobic ligand (e.g. the surface of beads). This interaction is usually so strong that it can occur in solutions of low ionic strength and is broken by the use of organic solvents (e.g. acetonitrile). Reversed phase chromatography can be used to fractionate complex protein samples and for desalting protein samples. RPC is usually performed using a solid phase packed in to a column. The beads of the invention enable the technique to be performed without a column, without sample dilution and to be automated with high throughput.

Hydrophobic interaction chromatography (HIC) is a separation technique that utilises a hydrophobic adsorption interaction between a solute molecule (e.g. a protein) and an immobilised hydrophobic ligand (e.g. the surface of beads). This interaction is weaker than the interactions utilised during RPC and requires promotion by high salt concentrations. Consequently, decreasing salt concentrations can be used to break these adsorption interactions. HIC can be used to fractionate complex protein samples and for desalting protein samples. HIC is usually performed using a solid phase packed in to a column. The beads of the invention enable the technique to be performed without a column, without sample dilution and to be automated with high throughput.

The invention will now be described further by reference to the following examples. These are not intended to be limitative but merely exemplary of the invention.

Example 1

Preparation of 0.3 μm Seed Particles 1600 g styrene was extracted with 2 L 10 wt. % sodium hydroxide, washed with water to pH 7 and then flushed with argon for 10 min. In a 10 L reactor, 8000 g of water and 3.07 g of borax were heated to 80° C., and 100 g of water was evaporated off to remove oxygen. Then 19.97 g sodium decyl sulphate in 200 ml boiled water was charged and stirred for 10 min. Then the washed and substantially oxygen-free styrene was charged and stirred for 15 min. Then 4.80 g potassium peroxodisulphate was charged in 200 g boiled water. The mixture was kept at 80° C. in an argon atmosphere for 13 hours. A monodisperse suspension of polymer particles was formed having a particle diameter of 0.3 μm.

Example 2

Preparation of 1.0 μm Polystyrene Particles 8860 g of water, 866 g DOP (dioctanoyl peroxide), 433 g acetone and 51.96 g of SDS were homogenized for 25 minutes in a two stage Manton Gaulin homogenizer at 400 kg/cm5 in the first stage and 100 kg/cm5 in the second stage. After homogenization, 5164 g of the emulsion were charged with a seed suspension of monodisperse polystyrene particles having a diameter of 0.3 μm from Example 1.1891 g of seed suspension containing 297.8 g of polymeric particles and 1593 g of water was used.

After stirring for 24 hours at 25° C., 6414 g of the activated seed particle suspension were charged with an emulsion containing 103400 g of water, 131 g of SDS (sodium dodecyl sulphate), 1556 g of polyvinylpyrrolidone K-30, 4157 g of 63.2% divinylbenzene, 1060 g styrene and 11606 g of toluene (as a porogen). The emulsion was homogenized for 25 mins at 400 kg/cm5 in the first stage and 100 kg/cm5 in the second stage.

After swelling for 2 hours at 25° C., 46676 g of water were charged to the reactor and then the dispersion was polymerized for 1 hour at 60° C. and 20 hours at 70° C. A monodisperse suspension was formed having a particle diameter of 1.0 μm.

The particles were washed with methanol and butylacetate and dried. By BET the specific surface area was determined to be 570 m5/g dry substance.

Example 3

Nitration

A mixture of 9920 g 95% sulphuric acid and 3020 g 65% nitric acid was cooled to 10° C. and then 400 g 1.0 μm dry porous crosslinked polystyrene particles from Example 2 were charged. The temperature was raised to 30° C. for 1 hour 30 min. The suspension was charged with 60 L ice and water. The particles were washed with water and methanol by filtration. The resulting particles contained 9.0 wt. % nitrogen.

Example 4

Incorporation of Iron 2579 g $FeSO_4.7H_2O$ and 3.2 g $MnSO_4.H_2O$ were added to a suspension of 4144 g nitrated porous particles from Example 3 containing 450 g of particles and 3694 g of water. The suspension was stirred at room temperature for 30 min. 3285 g of 25% $NH_3$ in water was added. The temperature was raised to 60° C. for 2 hours. The suspension was cooled and the particles were washed with water by centrifugation. After purification the particles were transferred to methanol. Analysis of the particles showed a content of 330 mg Fe/g DS (dry substance) and 0.9 mg Mn/g DS.

Example 5

Coating 133 g of a methanol suspension containing 13.3 g of 1.0 μm styrene-divinylbenzene polymer particles surface functionalized by nitration and reduction and containing superparamagnetic iron oxide (33 wt % Fe) were washed five times with 93 g diglyme. Dry substance of particles in diglyme was adjusted to 15 wt % and glycidol (3.07 g), 1,4-butanedioldiglycidylether (Araldite DY-026, 8.06 g) and glycidylmethacrylate (5.68 g) was added to the particles. The mixture was heated to 75° C. and stirred for 20 hours. The particles were then washed six times with 70 g methanol and four times with 80 g of isopropanol.

Example 6

Functionalisation with Carboxylic Acid Groups

To 1806 g of a suspension of the particles prepared in Example 5 (425 g) in isopropanol was added methanol (774 g), acrylic acid (514 g) and 2,2'-azoisobutyronitrile (23.4 g). The mixture was heated to 73-75° C. and stirred for 20 hours. The particles were then washed six times with 2338 g methanol and once with 3018 g of 0.15 M NaOH. The particle content (dry substance basis) was adjusted to 12 wt. % and the mixture was heated to 75° C. and stirred for 3.5 hours. The particles were washed three times with 3188 g water and five times with 3188 g 0.01 M NaOH.

47 g of a suspension of the particles prepared in Step (A) (13.3 g) in isopropanol was added methanol (24 g), acrylic acid (9.64 g) and 2,2'-azoisobutyronitrile (0.41 g). The mixture was heated to 73-75° C. and stirred for 20 hours. The particles were then washed six times with 73 g methanol and once with 94 g of 0.15 M NaOH. Dry substance of the mixture of particles and 0.15 M NaOH was adjusted to 12 wt % and the mixture was heated to 75° C. and stirred for 3.5 hours. The

Example 7

Functionalisation of carboxylic acid groups to N-hydroxysuccinimide ester 50 g of a suspension of 5.0 g of the particles of Example 6 were acidified by washing with 0.1 M acetic acid (3×50 mL). The acidified particles (which had a carboxylic acid content of 0.5 mmole/g DS) were then washed with acetone (4×50 mL) and concentrated on a magnet. Extra acetone was added until a total of 35.6 g suspension was achieved. N-hydroxysuccinimide (2.90 g, 25 mmole) and diisopropylcarbodiimide (3.16 g, 25 mmole) were then added. The reaction mixture was stirred at room temperature for 5 hours. The particles were then washed with acetone (5×50 mL).

Example 8

Immobilisation of Streptavidin 1. 20 mg of carboxylic acid functionalised beads of Example 6 were dispersed in 1 ml 0.01 M NaOH.
2. The beads were separated on a magnet and the supernatant discharged.
3. The beads were washed three times with 1 ml 30 mM 2-morpholino-ethanesulfonic acid (MES) pH 6.1.
4. 1.8 mg streptavidin dissolved in 900 μl 30 mM MES pH 6.1 was added to the beads.
5. The beads and streptavidin were incubated on mixing device at room temperature for 15 minutes.
6. 3 mg 1-ethyl-3-(3-dimethylaminopropyl)carbodiimide (EDC) dissolved in 75 μl cold distilled water was added.
7. The mixture was incubated on a mixing device at room temperature for one hour.
8. The beads were washed three times with Phosphate buffered saline (PBS) pH 7.4 with 0.01% (w/v) Tween 20 in order to remove excess streptavidin and EDC.
9. The beads were resuspended in PBS pH 7.4 with 0.1% Tween 20.

The amount of streptavidin was measured by use of tracer amounts of $I^{125}$-labelled streptavidin during coating. The relative amount of $I^{125}$-labelled streptavidin gives the amount of streptavidin coated to the surface.

Free biotin binding capacity was determined by addition of excess $C^{14}$-labelled biotin to the streptavidin coated beads. Excess biotin was washed away and the amount of $C^{14}$-biotin was measured using a beta-scintillation counter.

The amount of streptavidin coating was found to be 68 μg per mg beads, and the free biotin binding capacity was 3100 pmol free biotin per mg beads.

Example 9

Step A

To 40.0 g of 1.0 Φm styrenedivinylbenzene polymer particles containing superparamagnetic iron oxide (33 wt % Fe) (made analogously to Example 4) in 200 g diglyme, 100 g of 1,4-butanediol diglycidyl ether and 100 g of glycidol were added. The reaction mixture was stirred at 250 rpm for 20 hours at 90 EC. The particles were then washed five times with 400 mL methanol and four times with 400 mL deionised water.

particles was washed with three times with 99 g water and five times with 99 g 0.01 M NaOH.

Step B

To 72 g of an aqueous suspension of the particles prepared as in Step A (particle content 10 wt %), 119 g of sodium hydroxide was slowly added. 169.2 g of allyl glycidol ether was then added. After stirring at 250 rpm for 18 hours at 60 EC, the particles were washed five times with 1400 mL of methanol.

Example 10

To 10 g of 1.0 Φm styrenedivinylbenzene polymer particles containing superparamagnetic iron oxide (33 wt % Fe)(made analogously to Example 4) in 40 g diglyme, 16.7 g of allyl glycidyl ether, 16.8 g of 1,4-butanediol diglycidyl ether, and 16.8 g of glycidol were added. The reaction mixture was stirred at 300 rpm at 90 EC for 20 hours. The particles were then washed five times with 100 mL methanol.

Example 11

78 g of a diglyme suspension of 13 g of 1.0 μm styrenedivinylbenzene polymer particles surface functionalized by nitration and reduction and containing superparamagnetic iron oxide (33 wt % Fe) was added Desmodur VL (35.83 g), diethyleneglycol (2.82 g), tetraethyleneglycol (4.84 g). The mixture was heated at 80° C. and stirred for 21 hours.

A mixture of diethyleneglycol (47.04 g), tetraethylene glycol (80.45 g) and 1,4-diazabicyclo(2.2.2)octane (1.29 g) was added to the particle suspension. The mixture was heated at 80° C. and stirred for 2 hours. The particles were cooled and washed three times with 100 g diglyme and four times with 100 g of acetone.

Example 12

22 g of a methanol suspension of 1.0 μm styrene-divinylbenzene polymer particles surface functionalized by nitration and reduction and containing superparamagnetic iron oxide (33 wt % Fe) (made analogously to Example 4) were washed five times with 14 g diglyme. Dry substance of particles in diglyme was adjusted to 16 wt % and Araldite DY-026 (1,4-butanedioldiglycidylether) (26 g) and glycidol (26 g) was added to the particles. The mixture was heated to 90° C. and stirred for 20 hours. The particles were then washed 5 times with 80 g methanol and four times with 45 g of diglyme.

To 18 g of the diglyme suspension of particles was added methacrylic anhydride (15 g) and pyridine (0.4 g). The mixture was heated to 75° C. and stirred for 20 hours. The particles were then washed five times with 90 g methanol and three times with 60 g of isopropanol.

Example 13

124.45 gram of a diglyme suspension of 20 g of 1.0 μm styrene-divinylbenzene polymer particles surface functionalized by nitration and reduction and containing superparamagnetic iron oxide (33 wt % Fe) (made analogously to Example 4) was added 2,2-Bis[4-(glycidyloxy)phenyl]propane (Bisphenol A diglyidylether, Araldit LY-564) (42 g). The mixture was heated to 60° C. and stirred for 2 hours and the cooled to room temperature and stirred over night. The suspension was washed three times with diglyme and dry substance adjusted to 12%.

Glycidol (4.58 g), Araldit DY-026 (1,4-butanedioldiglycidylether) (12.1 g) and glycidylmethacrylate (8.57 g) were added. The mixture was heated at 75° C. and stirred for 21 hours. The particle suspension was cooled and the particles were washed six times with 100 g methanol and four times with 100 g of isopropanol.

Example 14

516 gram of a water suspension of 51.6 g of 1.0 μm styrene-divinylbenzene polymer particles surface functionalized by nitration and reduction and containing superparamagnetic iron oxide (33 wt % Fe) (375 g) was added solid sodium hydroxide (144.89 g), the mixture was stirred and temperature kept below 42° C. during the addition. Allylglycidylether (206.4 g) was added, and the mixture was heated to 60° C. stirred for 18 hours. The particle suspension was cooled and the particles were washed four times with 1500 g methanol.

Example 15

90 g of a methanol suspension of 15 g of 1.0 μm styrene-divinylbenzene polymer particles surface functionalized by nitration and reduction and containing superparamagnetic iron oxide (33 wt % Fe) (made analogously to Example 4) was washed three times with 60 g diglyme and 2,2-Bis[4-(glycidyloxy)phenyl]propane (Bisphenol A diglyidylether, Araldit LY-564) (70.40 g) and 1,4-butanedioldiglycidylether (Araldit DY-026) (4.61 g) added. The mixture was heated at 95° C. for 20 hours. The particles were cooled and washed three times with 100 g diglyme and three times with 100 g of methanol.

Example 16

To 23.48 g of a diglyme suspension of 5 g of 1.0 μm styrene-divinylbenzene polymer particles surface functionalized by nitration and reduction and containing superparamagnetic iron oxide (33 wt % Fe) (made analogously to Example 4) was added 2,2-Bis[4-(glycidyloxy)phenyl]propane (Bisphenol A diglyidylether, Araldit LY-564) (23.47 g) and polyethyleneglycoldiglycidylether Mw~300 (3.07 g). The mixture was heated at 95° C. for 20 hours. The particles were cooled and washed four times with 40 g of methanol.

Example 17

To 24.46 g of a diglyme suspension of 5 g of 1.0 μm styrene-divinylbenzene polymer particles surface functionalized by nitration and reduction and containing superparamagnetic iron oxide (33 wt % Fe) (made analogously to Example 4) was added 2,2-Bis[4-(glycidyloxy)phenyl]propane (Bisphenol A diglyidylether, Araldit LY-564) (23.54 g) and polyethyleneglycoldiglycidylether Mw~500 (15.28 g). The mixture was heated at 95° C. for 20 hours. The particles were cooled and washed five times with 40 g of methanol.

Example 18

To 26.82 g of a diglyme suspension of 5 g of 1.0 μm styrene-divinylbenzene polymer particles surface functionalized by nitration and reduction and containing superparamagnetic iron oxide (33 wt % Fe) (made analogously to Example 4) was added 2,2-Bis[4-(glycidyloxy)phenyl]propane (Bisphenol A diglyidylether, Araldit LY-564) (46.93 g) and glycerolpropoxylate triglycidylether (69.98 g). The mixture was heated at 95° C. for 20 hours. The particles were cooled and washed five times with 40 g of methanol.

Example 19

Immobilization of Streptavidin 20 mg of coated beads from Example 17 were dispersed in 1 ml 0.1 M Na-phosphate buffer pH 7.4. Beads were separated on a magnet and the supernatant discharged. This was repeated twice. 1 mg streptavidin dissolved in 900 ul 0.1 M Na-phosphate buffer pH 7.4 was added to the beads. Beads and streptavidin were incubated on a mixing device for 20 hours at room temperature. The beads were washed three times with PBS pH 7.4 with 0.1% BSA.

The free biotin binding capacity was measured as described in example 20 and found to be 1900 pmol free biotin per mg beads.

Example 20

Binding Capacity for Biotinylated DNA Molecules

1. Plasmid DNA fragments of 1090, 526, 217 base pairs were biotinylated and europium labelled by PCR.
2. The excess biotin and europium labels were removed by commercial PCR clean-up techniques and the labelled DNA quantified by optical density at 260 nm and time resolved fluorescence.
3. Streptavidin coated beads (Example 8) were washed once in a 2 times concentrated binding buffer (2M NaCl, 20 mM Tris HCl, 0.2M EDTA pH7.5).
4. 5 μg of the washed beads were resuspended in 100 μl of binding buffer in each well of a 96 well plate.
5. An excess of DNA (0.55 pmol of 1090 bp, 1.1 pmol of 526 bp and 2.2 pmol of 217 bp) diluted in 100 μl of water was added to the beads and incubated with gentle shaking for 15-30 minutes at room temperature.
6. The plate is placed on the magnet and the supernatant removed.
7. The beads-DNA complex are washed 3 times with 200 μl of wash buffer (10 mM Tris-HCl pH7.8, 0.01% Tween 20).
8. The beads-DNA complex are resuspended in 200 μl DELFIA Enhancement solution and incubated, protected from light, with shaking at room temperature for 10 minutes.
9. The plate is placed on the magnet and the Enhancement solution is transferred to a FluorNunc 96 well plate and the europium signal is measured by time resolved fluorescent (Wallac Victor plate reader) and given as counts per second (cps).
10. The DNA bound to the beads is calculated from the percent of cps added in 0.55, 1.1 and 2.2 pmol of DNA, that has bound to the beads.

The binding capacity of the beads is approximately 200 pmol/mg for the 217 bp fragment, 80-100 pmol/mg for the 526 bp fragment and 35-45 pmol/mg for the 1090 bp fragment.

Example 21

To 23.8 g of a diglyme suspension of 5 g of 1.0 μm styrene-divinylbenzene polymer particles surface functionalized by nitration and reduction and containing superparamagnetic iron oxide (33 wt % Fe) (made analogously to Example 4) was added Desmodur VL (18.34 g), diethyleneglycol (1.45 g), tetraethyleneglycol (2.48 g) and diglyme (36.2 g). The mixture was heated at 80° C. and stirred for 20 hours.

A mixture of polyethyleneglycol Mw~300 (68.24 g), tetraethylene glycol (41.30 g) and 1,4-diazabicyclo(2.2.2)octane (0.68 g) was added to the particle suspension. The mixture was heated at 80° C. and stirred for 1 hour. The particles were cooled and washed three times with 100 g diglyme and four times with 100 g of acetone.

Example 22

Immobilization of Immunoglobulin 20 mg of coated beads from Example 21 were dispersed in 1 ml 0.1 M Borate buffer pH 9.0. Beads were separated on a magnet and the supernatant discharged. This was repeated twice. 1 mg mouse IgG1 anti-human alpha feto protein dissolved in 900 ul 0.1 M Borate buffer pH 9.0 was added to the beads. Beads and antibody were incubated on a mixing device for 20 hours at room temperature. The beads were washed three times with PBS pH 7.4 with 0.1% BSA.

The amount of antibody bound to the beads was measured by the use of tracer amounts of I125-labelled antibody during coating. The relative amount of labelled antibody bound to the beads gives the total amount of antibody immobilized. Amount of protein immobilized to the beads was 22 µg antibody per mg beads.

The binding of alpha feto protein to the immobilized antibody was measured by addition of dilutions of umbilical cord blood and detected by use of a second mouse IgG anti-human alpha feto protein labelled with $Eu^{3+}$. The labelled antibody was detected with Time Resolved Fluorescence Spectroscopy. A standard curve dilution of the umbilical cord blood showed increased signal with increasing concentration.

Example 23

26.82 g of a diglyme suspension of 5 g of 1.0 µm styrene-divinylbenzene polymer particles surface functionalized by nitration and reduction and containing superparamagnetic iron oxide (33 wt % Fe) (made analogously to Example 4) was added Desmodur VL (18.34 g), polyethyleneglycol Mw~600 (15.84 g) and diglyme (33.20 g). The mixture was heated at 80° C. and stirred for 20 hours.

A mixture of polyethyleneglycol Mw~600 (263.82 g) and 1,4-diazabicyclo(2.2.2)octane (0.66 g) was added to the particle suspension. The mixture was heated at 80° C. and stirred for 1 hour. The particles were cooled and washed three times with 100 g diglyme and four times with 100 g of acetone.

Example 24

Functionalisation with Carboxylic Acid Groups

To 15.87 g of a suspension of the particles prepared in Example 5 (2.5 g) in isopropanol was added acrylic acid (1.84 g), acrylamide (1.79 g), methanol (5.95 g) and 2,2'-azoisobutyronitrile (0.28 g). The mixture was heated to 75° C. and stirred for 20 hours. The particles were then washed four times with 20 g isopropanol and 4 times with 25 g of 0.15 M NaOH.

Example 25

Functionalisation with Carboxylic Acid Groups

To 8.44 g of a suspension of the particles prepared Example 5 (1 g) in water was added acrylic acid (0.37 g), allylglycidylether (1.34 g), dimethylsulfoxide (0.91 g) and 2,2'-azoisobutyronitrile (0.06 g). The mixture was heated to 75° C. and stirred for 20 hours. The particles were then washed four times with 10 g isopropanol and 4 times with 10 g of 0.15 M NaOH.

Example 26

3.9 g of a diglyme suspension of 2.7 g of 1.0 µm styrene-divinylbenzene polymer particles surface functionalized by nitration and reduction and containing superparamagnetic iron oxide (33 wt % Fe) (made analogously to Example 4) was added hexamethylenediisocyanate (2.5 g), diethyleneglycol (0.5 g) and tetraethyleneglycol (1.0 g). The mixture was heated at 80° C. and stirred for 20 hours.

A mixture of diethylene glycol (2.65 g), tetraethylene glycol (4.66 g) and 1,4-diazabicyclo(2.2.2)octane (0.07 g) was added to the particle suspension. The mixture was heated at 95° C. and stirred for 2-3 hours. The particles were cooled and washed four times with 20 g acetone.

Example 27

23.8 g of a diglyme suspension of 5 g of 1.0 µm styrene-divinylbenzene polymer particles surface functionalized by nitration and reduction and containing superparamagnetic iron oxide (33 wt % Fe) (made analogously to Example 4) was added Desmodur VL (18.34 g), diethyleneglycol (1.45 g), tetraethyleneglycol (2.48 g) and diglyme (36.2 g). The mixture was heated at 80° C. and stirred for 20 hours.

A mixture of polyethyleneglycol Mw~400 (90.03 g), tetraethylene glycol (41.20 g) and 1,4-diazabicyclo(2.2.2)octane (0.68 g) was added to the particle suspension. The mixture was heated at 80° C. and stirred for 1 hour. The particles were cooled and washed three times with 100 g diglyme and four times with 100 g of acetone.

Example 28

23.8 g of a diglyme suspension of 5 g of 1.0 µm styrene-divinylbenzene polymer particles surface functionalized by nitration and reduction and containing superparamagnetic iron oxide (33 wt % Fe) (made analogously to Example 4) was added Desmodur VL (18.34 g), diethyleneglycol (1.45 g), tetraethyleneglycol (2.48 g) and diglyme (36.2 g). The mixture was heated at 80° C. and stirred for 20 hours.

A mixture of polyethyleneglycol Mw~600 (135 g), tetraethylene glycol (41.30 g) and 1,4-diazabicyclo(2.2.2)octane (0.66 g) was added to the particle suspension. The mixture was heated at 80° C. and stirred for 1 hour. The particles were cooled and washed three times with 100 g diglyme and four times with 100 g of acetone.

Example 29

23.8 g of a diglyme suspension of 5 g of 1.0 µm styrene-divinylbenzene polymer particles surface functionalized by nitration and reduction and containing superparamagnetic iron oxide (33 wt % Fe) (made analogously to Example 4) was added Desmodur VL (18.34 g), diethyleneglycol (1.45 g), tetraethyleneglycol (2.48 g) and diglyme (36.2 g). The mixture was heated at 80° C. and stirred for 20 hours.

A mixture of ethyleneglycol (27.29 g) and 1,4-diazabicyclo(2.2.2)octane (0.66 g) was added to the particle suspension. The mixture was heated at 80° C. and stirred for 1 hour. The particles were cooled and washed three times with 100 g diglyme and four times with 100 g of acetone.

Example 30

26.82 g of a diglyme suspension of 5 g of 1.0 µm styrene-divinylbenzene polymer particles surface functionalized by nitration and reduction and containing superparamagnetic iron oxide (33 wt % Fe) (made analogously to Example 4) was added Desmodur VL (18.34 g) and ethyleneglycol (1.64 g). The mixture was heated at 80° C. and stirred for 20 hours. A mixture of ethyleneglycol (27.29 g) and 1,4-diazabicyclo (2.2.2)octane (0.66 g) was added to the particle suspension. The mixture was heated at 80° C. and stirred for 1 hour. The particles were cooled and washed three times with 100 g diglyme and four times with 100 g of acetone.

Example 31

Activation with Tosyl Groups

To 17.1 g of an acetone suspension of 4 g of Example 30 were added tosylchloride (16 g) and pyridine (7.85 g). The mixture was stirred at 25° C. for 17 hours. The particles was then washed three times with 50 ml acetone, once with 50 ml of a mixture of 80% by weight of acetone in water, once with 50 ml of a mixture of 60% by weight of acetone in water, once with 50 ml of a mixture of 30% by weight of acetone in water and three times with 50 ml water.

Example 32

Immunoassay for Alpha Feto Protein 50 ug of immunoglobulin coated beads from example 22 was added to 100 ul of dilutions of umbilical cord blood and the content of Alpha Feto Protein allowed to bind during incubation for 15 minutes. Excess umbilical cord blood was washed away. To this complex a second detection mouse IgG anti-human alpha feto protein labelled with $Eu^{3+}$ was added. After incubation and removal of excess detection antibody the amount of labelled antibody was detected with Time Resolved Fluorescence Spectroscopy. A standard curve dilution of umbilical cord blood with known amount of Alpha Feto Protein showed increased signal with increasing concentration. By use of this standard curve the amount of Alpha Feto Protein in samples could be determined.

Example 33

Immunoassay for Myoglobulin

Beads coated similarly as in example 22, but with mouse IgG anti-human myoglobulin were used to analyse the content of Myoglobulin in human citrated plasma samples on a Liaison immunoassay instrument. Beads and samples (10 ul) were incubated for 10 minutes and excess sample washed away. Detection antibody conjugated with Acridinium orange ester was added. After incubation for 10 minutes excess detection antibody was washed away, and the chemiluminescent signal was developed and detected in the luminescence reader in the Liaison instrument.

Example 34

Immunoassay for D-Dimer

Beads coated similarly as in example 22, but with mouse IgG anti-human D-dimer were used to analyse the content of Myoglobulin in human citrated plasma samples on a Liaison immunoassay instrument. Beads and samples (10 ul) were incubated for 10 minutes and excess sample washed away. Detection antibody conjugated with Acridinium orange ester was added. After incubation for 10 minutes excess detection antibody was washed away, and the chemiluminescent signal was developed and detected in the luminescence reader in the Liaison instrument.

Example 35

Immunoassay for Intact PTH

Beads coated with streptavidin as in example 19 were used to analyse the content of intact PTH in samples of human EDTA plasma on a Liaison immunoassay instrument. 150 ul of EDTA plasma was incubated with a biotinylated polyclonal goat antibody raised against intact PTH, and an acridinium ester conjugated polyclonal goat antibody raised similarly to yield an immunocomplex. The streptavidin coated beads was added to the immunocomplex and incubated to allow the biotin to bind to the immobilized streptavidin. The beads were washed and the chemiluminescent signal developed and measured in the luminescence reader in the Liaison instrument.

Example 36

22 g of a methanol suspension of 1.0 µm styrene-divinylbenzene polymer particles surface functionalized by nitration and reduction and containing superparamagnetic iron oxide (33 wt % Fe) (made analogously to Example 4) were washed five times with 14 g diglyme. Dry substance of particles in diglyme was adjusted to 16 wt % and glycidylmethacrylate (50 g) and Iron (III) chloride (0.62 g) was added to the particles. The mixture was heated to 75° C. and stirred for 20 hours. The particles were then washed six times with 14 g methanol and four times with 13 g of isopropanol.

Example 37

26.82 g of a diglyme suspension of 5 g of 1.0 µm styrene-divinylbenzene polymer particles surface functionalized by nitration and reduction and containing superparamagnetic iron oxide (33 wt % Fe) (made analogously to Example 4) was Desmodur VL 18.34 g) and diglyme (33.20 g). The mixture was heated at 80° C. and stirred for 20 hours. A mixture of polyethyleneglycol Mw~600 (236.82 g) and 1,4-diazabicyclo(2.2.2)octane (0.66 g) was added to the particle suspension. The mixture was heated at 80° C. and stirred for 1 hour. The particles were cooled and washed three times with 100 g diglyme and four times with 100 g of acetone.

Example 38

10.74 g of a diglyme suspension of 2 g of 1.0 µm styrene-divinylbenzene polymer particles surface functionalized by nitration and reduction and containing superparamagnetic iron oxide (33 wt % Fe) (made analogously to Example 4) was added glycidol (6.84 g). The mixture was heated at 90° C. for 20 hours. The particles were cooled and washed eight times with 17 g of methanol and four times with 17 g of water.

Example 39

14.52 g of a diglyme suspension of 2.50 g of 1.0 µm styrene-divinylbenzene polymer particles surface functionalized by nitration and reduction and containing superparamagnetic iron oxide (33 wt % Fe) (made analogously to Example 4) was added 2,2-Bis[4-(glycidyloxy)phenyl]propane (Bisphenol A diglyidylether, Araldit LY-564) (13.03 g). The mixture was heated at 95° C. for 20 hours. The particles were cooled and washed three times with 17 g of diglyme and five times with 17 g of methanol.

Example 40

Binding Capacity for Biotinylated Protein Molecules 1. 5 μg of the streptavidin beads (Ex 19) were washed once in DELFIA assay buffer and mixed with an excess of biotinylated antibody labelled with europium$^{3+}$ in a 96 well plate.
2. Incubation with mixing at room temperature was carried out for 20 minutes to allow the antibody to bind to the beads.
3. The plate was placed on the magnet and the supernatant removed.
4. The beads-antibody complex were washed 3 times with 200 μl of DELFIA wash buffer
5. The beads-antibody complex were resuspended in 200 μl DELFIA Enhancement solution and incubated, protected from light, with shaking at room temperature for 10 minutes.
6. The plate was placed on the magnet and the enhancement solution is transferred to a FluorNunc 96 well plate and the europium signal measured by time resolved fluorescent (Wallac Victor plate reader) and given as counts per second (cps).
7. The amount of antibody bound to the beads was calculated from the percent of cps added that has bound to the beads.

The binding capacity of the beads was approximately 8.0 μg biotinylated antibody per mg beads.

Example 41

30.1 g of a diglyme suspension of 5 g of 1.0 μm styrene-divinylbenzene polymer particles surface functionalized by nitration and reduction and containing superparamagnetic iron oxide (33 wt % Fe) was added Desmodur VL (13.8 g), diethyleneglycol (2.08 g). The mixture was heated at 80° C. and stirred for 20 hours. A mixture of diethyleneglycol (35 g) and 1,4-diazabicyclo(2.2.2)octane (0.5 g) was added to the particle suspension. The mixture was heated at 80° C. and stirred for 1 hour. The particles were cooled and washed three times with 80 ml diglyme and five times with 80 ml of acetone.

Example 42

30.8 g of a diglyme suspension of 5 g of 1.0 μm styrene-divinylbenzene polymer particles surface functionalized by nitration and reduction and containing superparamagnetic iron oxide (33 wt % Fe) was added Desmodur VL (13.8 g). The mixture was heated at 80° C. and stirred for 20 hours. A mixture of diethyleneglycol (35 g) and 1,4-diazabicyclo (2.2.2)octane (0.5 g) was added to the particle suspension. The mixture was heated at 80° C. and stirred for 1 hour. The particles were cooled and washed three times with 80 ml diglyme and five times with 80 ml of acetone.

Example 43

7.0 g of 1.0 μm styrene-divinylbenzene polymer particles surface functionalized by nitration and reduction and containing superparamagnetic iron oxide (33 wt % Fe) was adjusted to 20 weight percent dry material in diethylene glycol dimethylether. 17.5 g Araldit Dy-026 and 17.5 g Glycidol was added to the suspension, and the mixture was heated at 90° C. for 20 hours. The beads were washed five times with methanol (200 ml) and five times with water (200 ml).

Example 44

To a 80 g of a suspension of 8.0 g beads in example 43 was added 22.5 g sodium hydroxide and 32 g of allylglycidylether. The beads were stirred and heated at 60° C. for 18 hours, and worked up by washing with four times with 240 methanol.

Example 45

Reversed Phase Chromatography (RPC)

The beads of examples 41, 42, 11, 15, and 30 were used to fractionate a protein mixture consisting of conalbumin, soya bean trypsin inhibitor, alcohol dehydrogenase, cytochrome C and diamine oxidase, or cell lysates from SW 480 cells. 1 mg of beads were pre-washed and resuspended in 10 ul of an RPC adsorption buffer (obtained from Bruker Daltonics or alternatively 50 mM sodium phosphate buffer, 1 M ammonium sulphate, 0.1% trifluoroacetic acid) and incubated with 25 ug of the protein mixture or cell lysate for 1 minute. Following adsorption, the beads were washed three times with washing buffer (obtained from Bruker Daltonics or 50 mM sodium phosphate buffer, 1 M ammonium sulphate, 0.1% trifluoroacetic acid) and the proteins subsequently desorbed in fractions by the use of desorption buffers containing increasing concentrations of acetonitrile (0, 15, 30, 40 & 50%)

Example 46

Hydrophobic Interaction Chromatography (HIC)

The beads of Example 44 were used to fractionate a protein mixture consisting of conalbumin, soya bean trypsin inhibitor, alcohol dehydrogenase, cytochrome C and diamine oxidase. 1 mg of beads were pre-washed and resuspended in adsorption buffer (50 mM sodium phosphate buffer pH 5.8, 1 M ammonium sulphate) and incubated with 25 g of the protein mixture for 1 minute. Following adsorption, the beads were washed three times with an appropriate washing buffer (50 mM sodium phosphate buffer, 1 M ammonium sulphate) and the proteins subsequently desorbed in fractions using desorption buffers containing decreasing concentrations of ammonium sulphate (0.8, 0.6, 0.4, 0.2 & 0.0 M).

Example 47

26.81 g of a diglyme suspension of 5 g of 1.0 μm styrene-divinylbenzene polymer particles surface functionalized by nitration and reduction and containing superparamagnetic iron oxide (46 wt % Fe) (375 g) was added Desmodur VL (18.39 g) and diglyme (33.50 g). The mixture was heated at 80° C. and stirred for 20 hours. The particles were cooled and washed three times with 100 g of dimethylformamide and added 2,2 (ethylenedioxide)-diethylamine (74.4 g) and 1,4-diazabicyclo(2.2.2)octane (0.63 g). The mixture was heated to 80° C. for two hours. The particles were cooled and washed four times with 100 g dimethylformamide.

6.66 g of this dimethylformamide suspension was added 1,4-butanedioldiglycidylether (Araldit LY-026) (3.03 g). The mixture was heated to 70° C. for 20 hours. The particles were cooled and washed three times with 17 g of dimethylformamide.

The invention claimed is:
1. A process for the preparation of coated polymer particles containing superparamagnetic crystals, the process comprising reacting porous, surface-functionalized, superparamag- netic crystal-containing polymer particles of diameter 0.5 to 1.8 μm with at least two epoxide compounds, at least one of which having an unsaturated carbon-carbon bond copolymerizable with an acrylic monomer; and reacting the formed particles with an acrylic monomer.

2. The process of claim 1, wherein the acrylic monomer is acrylic acid.

3. The process of claim 1, wherein the acrylic monomer is acrylamide.

4. The process of claim 1, wherein the acrylic monomer is reacted with N-hydroxysuccinimide or with streptavidin.

5. The process of claim 1, wherein at least one of the at least two epoxide compounds is a bisepoxide compound.

6. The process of claim 1, wherein the at least two epoxide compounds are selected from the group consisting of glycidol and 1,4-bis-(2,3-epoxypropoxy)butane.

7. The process of claim 1, wherein the at least two epoxide compounds are selected from the group consisting of 1,4-bis-(2,3-epoxypropoxy)butane and 2,2-bis(4-(2,3-epoxypropoxy)phenyl)-propane.

8. The process of claim 1, wherein the at least two epoxide compounds are selected from the group consisting of glycidol, allylglycidyl ether and 1,4-bis-(2,3-epoxypropoxy)butane.

9. The process of claim 1, wherein one of the at least two epoxide compounds has a molecular weight of 150 g/mol to 1000 g/mol.

* * * * *